United States Patent [19]

Utsugi

[11] 4,198,958

[45] Apr. 22, 1980

[54] FLEXIBLE CAP AND INSTRUMENT SEAL FOR A SUCTION CONTROL DEVICE IN AN ENDOSCOPE

[75] Inventor: Mikio Utsugi, Machida, Japan

[73] Assignee: Olympus Optical Co., Ltd., Tokyo, Japan

[21] Appl. No.: 909,984

[22] Filed: May 26, 1978

[30] Foreign Application Priority Data

Jun. 1, 1977 [JP] Japan .................................. 52-71197

[51] Int. Cl.² ............................................... A61B 1/00
[52] U.S. Cl. ......................................... 128/5; 128/276
[58] Field of Search ........................................ 128/3–8, 128/276–278, 297, 9–11

[56] References Cited

U.S. PATENT DOCUMENTS

| | | | |
|---|---|---|---|
| 3,162,195 | 12/1964 | Dick | 128/276 |
| 3,958,566 | 5/1976 | Furihata | 128/4 |
| 4,013,310 | 3/1977 | Dye | 128/276 UX |

FOREIGN PATENT DOCUMENTS

2350945  5/1974  Fed. Rep. of Germany ........... 128/276

*Primary Examiner*—Robert W. Michell
*Assistant Examiner*—Jeffrey W. Tayon

[57] ABSTRACT

A suction control device for an endoscope comprises an outer tube assembly having one end connected to the proximal end of the endoscope and an inner tube assembly coaxially inserted into the outer tube assembly. The inner tube assembly leads an elongated medical instrument therethrough to a channel in the endoscope. An air chamber is defined between the outer tube assembly and the inner tube assembly and communicates with the channel in the endoscope and with a suction pipe fixed to the outer tube. The proximal ends of the inner tube assembly and the outer tube assembly are covered with a flexible cap of a flexible material which is provided with an air inlet communicating with the inner tube assembly and another air inlet disposed near the first air inlet for communication with the air chamber such that both air inlets can be simultaneously blocked by a finger cushion. Provided in the inner tube assembly is a sealing member made of rubber having a central aperture with a diameter smaller than that of the medical instrument passing through it. The flexibility of the cap enables the finger to completely block the air inlets, and the close arrangement of the air inlets provides their simultaneously easy blocking by a single finger. Moreover, the sealing member assures a fluid tightness between the channel and the inner tube assembly.

4 Claims, 7 Drawing Figures

FIG. 4
FIG. 3
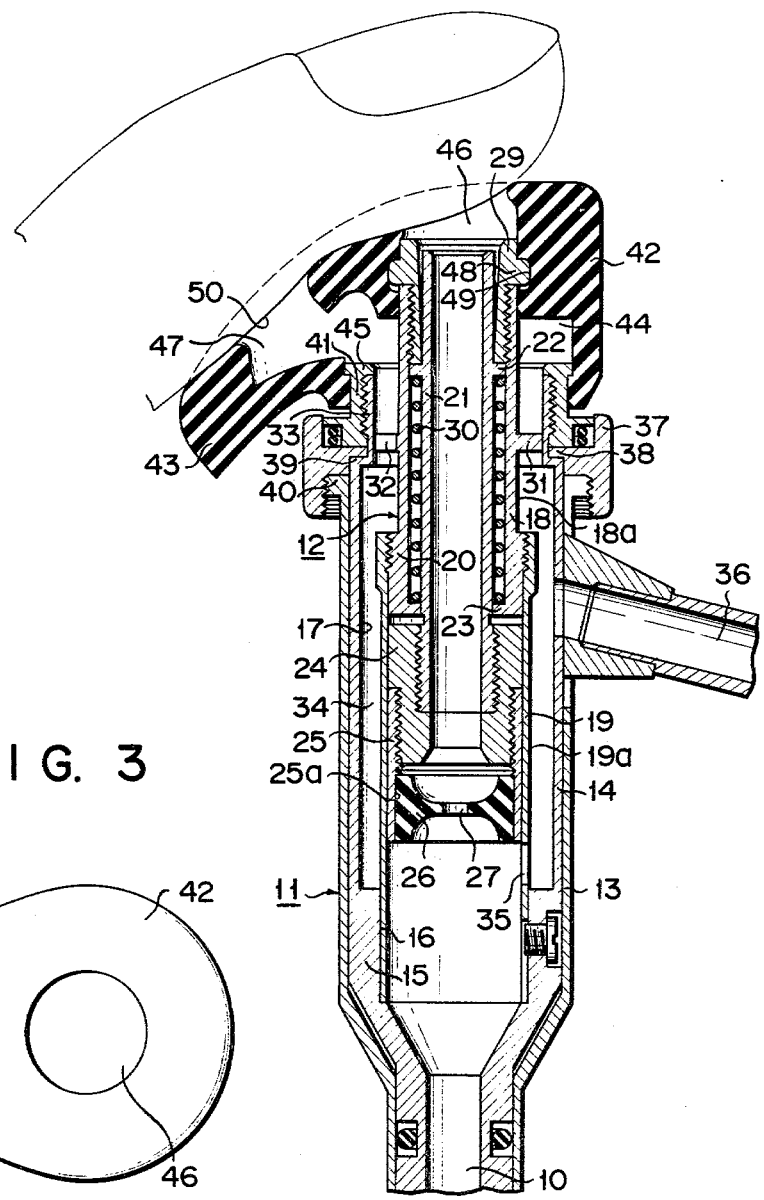
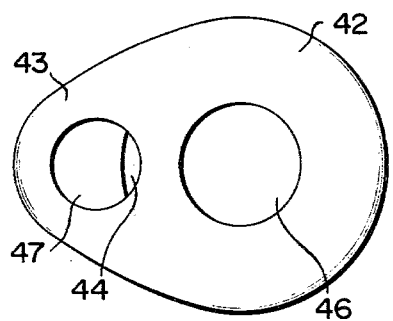

FLEXIBLE CAP AND INSTRUMENT SEAL FOR A SUCTION CONTROL DEVICE IN AN ENDOSCOPE

BACKGROUND OF THE INVENTION

This invention relates to a suction control device in an endoscope, which is used to remove mucus, dirty substance or the like in the human body cavity through an endoscope channel.

Generally, a suction control device in an endoscope serves, in addition to the original function of controlling the sucking out of mucus, dirty substance etc. in the human body cavity, to lead a medical fluid, as well as a medical instrument such as forceps, into the channel of the endoscope. A conventional suction control device for an endoscope comprises, as shown in FIG. 1, a mounting tube 1 provided on the operating section 2 of the endoscope, a hollow cylindrical member 3 tightly fitted into the mounting tube 1 and having its distal end communicating with a corresponding channel of the endoscope, and an inner tube assembly 4 coaxially inserted into the hollow cylindrical member 3. An air chamber 5 is defined by the inner surface of a larger diameter portion of the hollow cylindrical member 3 and outer surface of the inner tube assembly 4 and communicates with the endoscope channel and with a suction tube 6 projecting from the side wall of the hollow cylindrical member 3. A metallic cap 7 is fitted over the proximal end of the hollow cylindrical member 3 and has a central hole 8 communicating with the interior of the inner tube assembly 4. The central hole 8 of the cap 7 is adapted to be blocked by a finger cushion so as to take out through the endoscope channel, mucus, dirty substances etc. in the body cavity of the human being. Since, however, the cap of the conventional control device is made of metal, no sufficient contact is assured between the inner peripheral edge of the central hole 8 of the cap 7 and the finger cushion. In other words, air leaks into the inner pipe assembly 4 from between the inner peripheral edge of the central hole 8 of the cap 7 and the finger cushion, failing to sufficiently remove mucus, dirty substance etc. from the human body cavity. It is a usual practice to operate various levers of the endoscope operating section 2 by the thumb and block the central hole 8 of the cap by the index finger of the same hand. Since, however, the cap 7 lacks flexibility, it is not easy for the user to quickly block the control hole 8 of the cap 7 as required. The mere placement of the index finger over the central hole 8 of the cap 7 is sometimes insufficient to completely block the central hole 8 of the cap 7. Furthermore, where an elongated medical instrument such as forceps is used, the central hole 8 of the cap 7 can not be blocked by the human finger, since the instrument is inserted into the inner pipe assembly 4. As a result, a sucking capability is markedly reduced.

SUMMARY OF THE INVENTION

It is accordingly the object of this invention to provide a suction control device in an endoscope, in which air inlets of the cap can be readily, quickly and positively blocked by the finger cushion during a suction operation, and in which, even when an elongated medical instrument including forceps is inserted into the endoscope, a suction operation can be positively controlled.

According to this invention, there is provided a suction control device in an endoscope, comprising an outer tube assembly having one end connected to the proximal end of the endoscope, an inner tube assembly coaxially inserted into the outer tube assembly, an air chamber defined between the inner and outer tube assemblies communicating with the interior of a distal end portion of the inner tube assembly, an air suction pipe extending from the lateral wall of the outer tube assembly and communicating with the air chamber, a flexible cap mounted on the proximal end of the outer tube assembly, a first air inlet formed in the cap for conducting air into the inner tube assembly, a second air inlet formed in the cap for conducting air into the air chamber, and a sealing means provided in the inner tube assembly for sealing the interior of the distal end portion of the inner tube assembly from the interior of the proximal end thereof.

BRIEF DESCRIPTION OF THE DRAWINGS

FIG. 3 shows a plan view of a cap of FIG. 2;

FIG. 4 shows a longitudinal cross sectional view of the same embodiment as of FIG. 1 with a finger cushion pressed against air inlets of a cap of the device;

DESCRIPTION OF THE PREFERRED EMBODIMENTS

Figure 1:
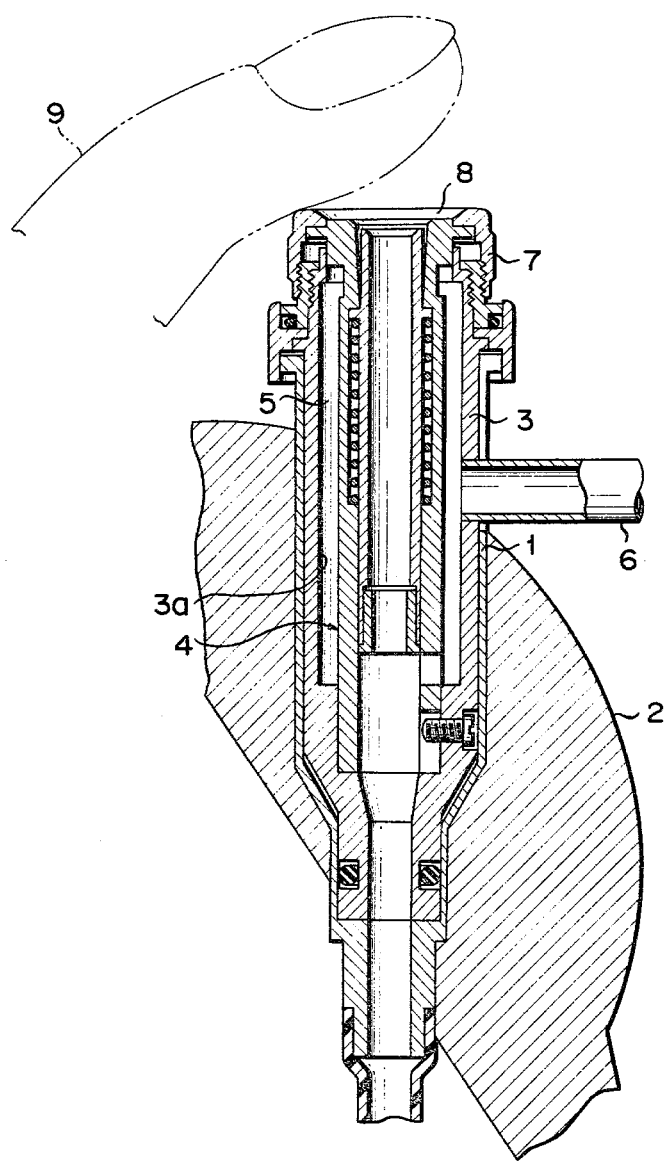
FIG. 1 shows a longitudinal sectional view of a prior art suction control device in an endoscope.

Like reference numerals are employed to designate identical or similar parts or elements throughout the specification and, with respect to parts or elements already explained in a preceding embodiment, further explanation will be omitted so as to avoid unnecessary duplication.

Figure 2:
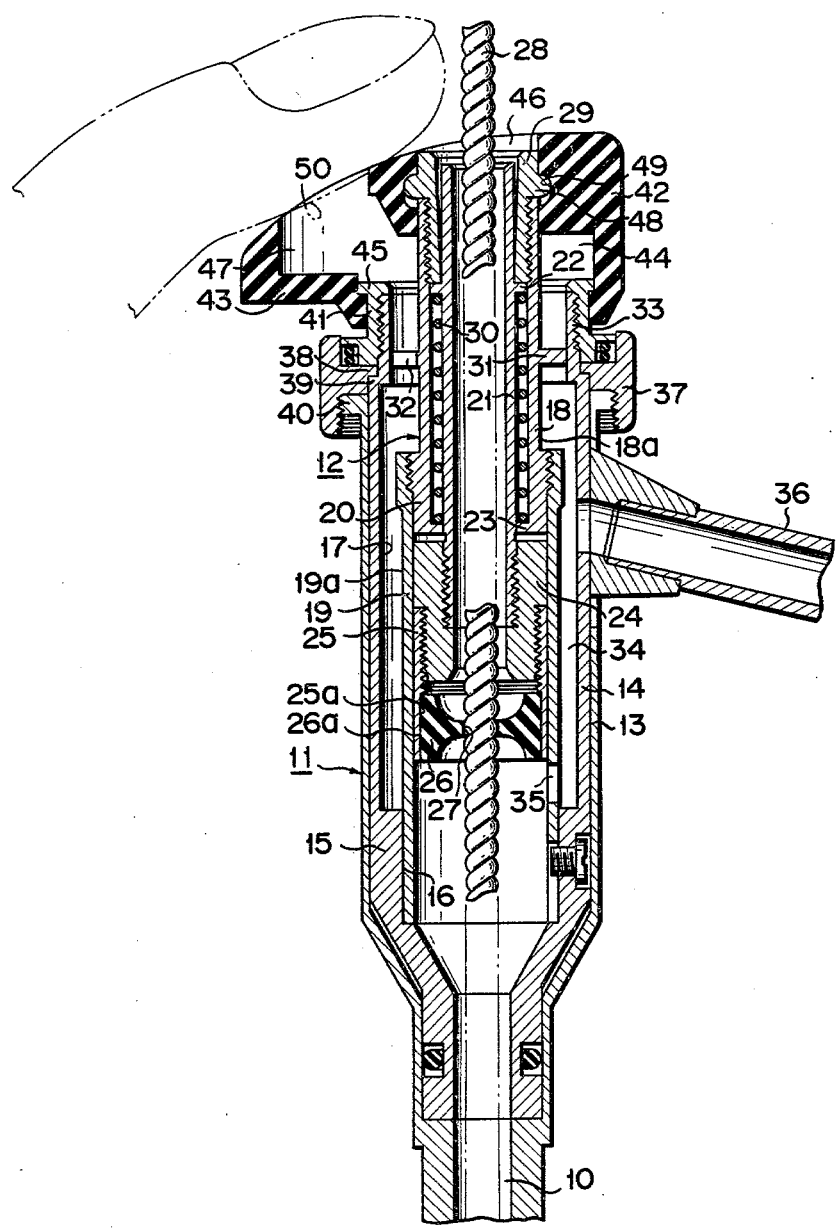
FIG. 2 shows a longitudinal cross sectional view of an embodiment of this invention with an elongated medical instrument inserted thereinto.
Figure 5:
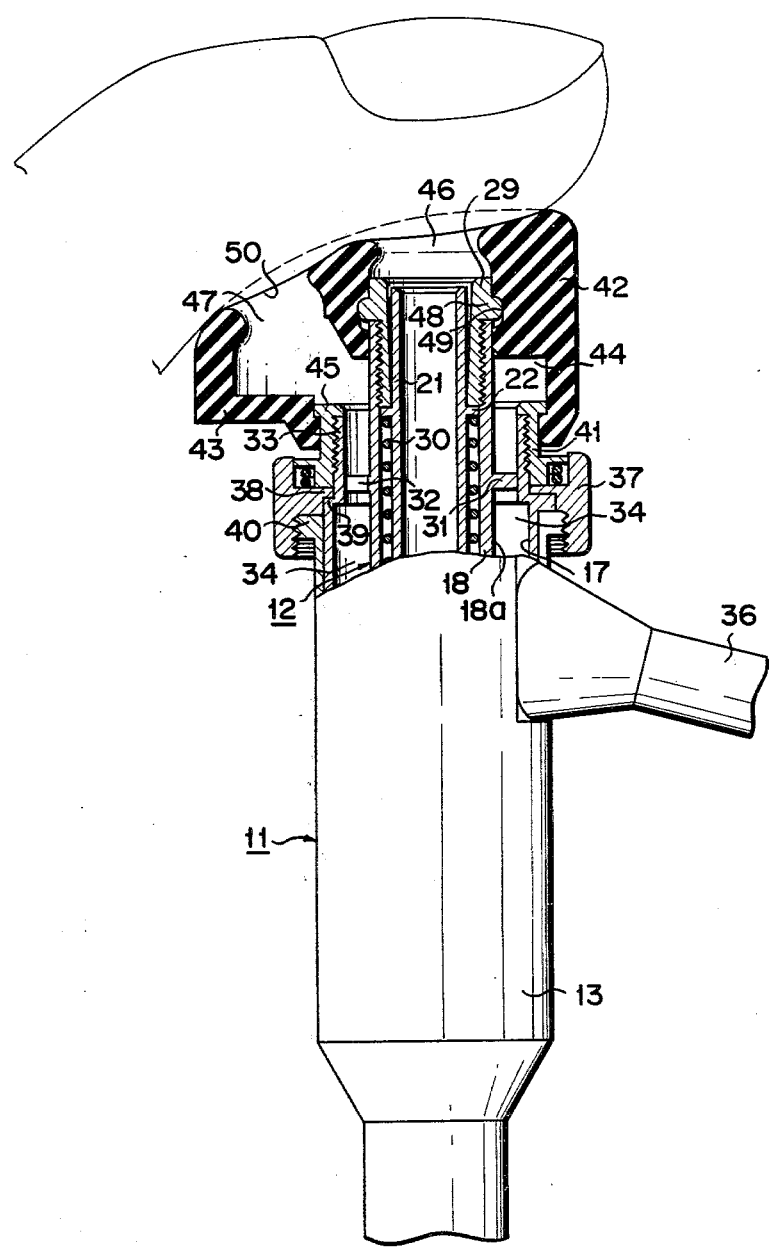
FIG. 5 shows a partially broken front view of the same embodiment as of FIG. 1 with a finger cushion pressed against air inlets of a cap of the device in a manner different from that of FIG. 3.

Referring to FIGS. 2, 4 and 5 a suction control device for an endoscope comprises an outer tube assembly 11 and an inner tube assembly 12 coaxially inserted into the outer tube assembly 11. The outer tube assembly 11 comprises a metallic mounting tube 13 placed in an operating section (not shown) of an endoscope and having its distal end connected to an endoscope channel 10, and a metallic hollow cylindrical member 14 inserted into the mounting tube 13. At the distal end portion of the member 14 is formed an annular stepped portion 15 having a central hole 16 smaller than the inner diameter of the remaining major portion of the cylindrical member 14. The inner tube assembly 12 comprises a first metallic tubular member 18 at the "proximal end" side and a second metallic tubular member 19 having its distal end inserted into the central hole 16 of the annular stepped portion 15 and its proximal end threadably engaging the larger diameter portion 20 formed on the distal end of the first tubular member 18. A metallic inner tube 21 is inserted into the first tubular member 18 and has an outwardly extending flange 22 formed on its intermediate outer surface. The flange 22 is slidably engaged at its outer surface with the inner surface of the member 18 and the unflanged intermediate outer surface portion of the inner tube 21 is adapted to be slidably engaged with a flange 23 inwardly extending from the end of the larger diameter portion 20 of the first tubular member 18. The distal end of the inner tube 21 is screwed into a metallic hollow cylindrical connection member 24 which is inserted into the second tubular member 19. A metallic sleeve 25 is slidably inserted into the second tubular member 19. The "proximal end" half portion of the sleeve 25 is screwed on the "distal end" portion of the connection member 24. An elastic sealing member 26 is fixed to or pressed into the distal end side half portion of the sleeve 25, so that the inner surface 25a of the sleeve 25 and the outer surface 26a of the sealing member 26 closely contact each other. The sealing member 26 is made of, for example, rubber or a flexible plastic material and has a substantially H shape in longitudinal cross section. A central aperture 27 is formed in the horizontal bar portion of said H shape of the sealing member 26 and extends perpendicular to said horizontal bar portion and has an inner diameter smaller than the outer diameter of an elongated medical instrument 28, such as forceps, to be inserted, as required, into the endoscope channel 10 through the inner tube 21. With the medical instrument 28 inserted as shown in FIG. 2, the sealing member 26 assures a fluid-tightness between the inner tube assembly and the endoscope channel.

Provided between the proximal end portions of the first tubular member 18 and the inner tube 21 is a metallic stop ring 29 which is screwed on the first tubular member 18. Between the flange 22 of the inner tube 21 and the flange 23 of the first tubular member 18, a compression spring 30 is wound around the inner tube 21. When the flange 22 of the inner tube 21 is pressed by the compression spring 30, the inner tube 21, connection member 24, sleeve 25 and sealing member 26 are elastically urged as a unit toward the proximal end of the control device. A flange 31 is formed on the intermediate outer surface of the first tubular member 18. In the flange 31, a circumferentially spaced-apart passages 32 are formed. The outer surface of the flange 31 is contacted by a reduced diameter surface 33 of the "proximal end" portion of the hollow cylindrical member 14. The flange 31 coacts with an annular stepped portion 15 to hold the inner tube assembly 12 in a concentric relation to the hollow cylindrical member 14. A hollow cylindrical air chamber 34 is defined between the outer surface of the tubular members 18, 19 (i.e. the outer surface of the inner assembly) and the inner surface 17 of the hollow cylindrical member 14. The chamber 34 communicates with the endoscope channel 10 through a hole 35 formed in that "distal end" portion of the second tubular member 19 which is located close to the sealing member 26. The chamber 34 also communicates with a suction pipe 36 extending from the hollow cylindrical member 14 and having its free end connected to a suction device (not shown).

A mounting ring 37 has a disc portion 38 provided at the substantially middle portion thereof and engaged with a shoulder 39 provided between the reduced diameter portion 33 and the unreduced portion of the hollow cylindrical member 14. The ring 37 has a first section at the "distal end" side and a second section at the "proximal end" section with the disc portion 38 in the middle. The first section of the ring 37 is screwed on a flange 40 formed on the proximal end portion of the mounting tube 13 and the second section of the ring 37 has the distal end portion of a connector 41 inserted thereinto.

The connector 41 is screwed over the reduced diameter portion 33 of the hollow cylindrical member 14. In consequence, the hollow cylindrical member 14 is fixed by the ring 37 and connector 41 to the mounting tube 13.

In FIGS. 2 to 5, a cap 42 made of a flexible material such as rubber or flexible plastic takes a form of a saddle in a longitudinal cross section and oval shape in the plan view, having an overhanging portion 43. The cap 42 includes a substantially cylindrical communication chamber 44 having an inner diameter substantially equal to the outer diameter of a flange 45 formed on the proximal end of the connector 41, a first air inlet 46 into which the proximal end of the first tubular member 18 is inserted, and a second air inlet 47 provided in the overhanging portion 43 thereof and communicating with the chamber 44. The distal end of the cap 42 is elastically pressed against the outer surface of the connector 41 clear of the flange 45 of the connector 41. At the inlet 46, the cap 42 closely contacts the proximal end portion of the first tubular member 18 and the stop ring 29 with a flange 48 on the outer lateral surface of the stop ring 29 fitted in an annular groove 49 in the inner wall of the air inlet 46. Thus, the cap 42 is sealingly provided on the proximal end of the control device except for the air inlets 46, 47. The size and spacing of both the air inlets 46, 47 are such that the air inlets 46 and 47 can be positively blocked by a finger cushion 50.

The operation of the suction control device will now be described below.

Where a medical instrument 28 such as a forceps 28 is not inserted into the control device, let both the air inlets 46 and 47 be blocked by the finger cushion 50. Then, a negative pressure is built up by the suction device in the channel 10 which communicates with the air chamber 34 through the hole 35. As a result, mucus and dirty substance are sucked out of the body cavity of the human being. Since both the air inlets 46 and 47 are arranged adjacent to each other, they can be advantageously blocked simultaneously by the cushion of a single finger such as an index finger. As the cap 42 is made of a flexible material, the air inlets 46 and 47 can be completely blocked by the finger cushion, thereby preventing leakage of air. Suppose that the inclination angle of the finger with respect to the cap 42 varies, as shown in FIGS. 4 and 5. Even in this case, the deformable overhanging portion 43 can be bent according to the inclination angle to thereby block the air inlets 46, 47 in an airtight relation.

Now suppose that the medical instrument 28, such as forceps, are inserted through the first air inlet 46. Since, in this case, the inner surface of the central hole 27 sealingly contacts the outer surface of the instrument 28, no air is introduced through the first air inlet 46 into the channel 10 and thus a suction operation can be effected only by blocking the second air inlet 47 by means of the finger cushion 50.

Where an injecting apparatus is employed, the proximal end of the inner tube 21 is pressed by the forward end of the injecting apparatus so that the inner tube assembly 12 is lowered until the outer surface of the sleeve 25 blocks the hole 35 in the second tubular member 19. Then, material to be injected is pushed out from the injecting apparatus into the human body cavity through the suction control device 11 and the channel 10. Since the hole 35 is blocked by the sleeve 25 in this case, the material to be injected does not flow from the central bore defined by the distal end side inner surface of the second tubular member 19 into the chamber 34.

Figure 6:
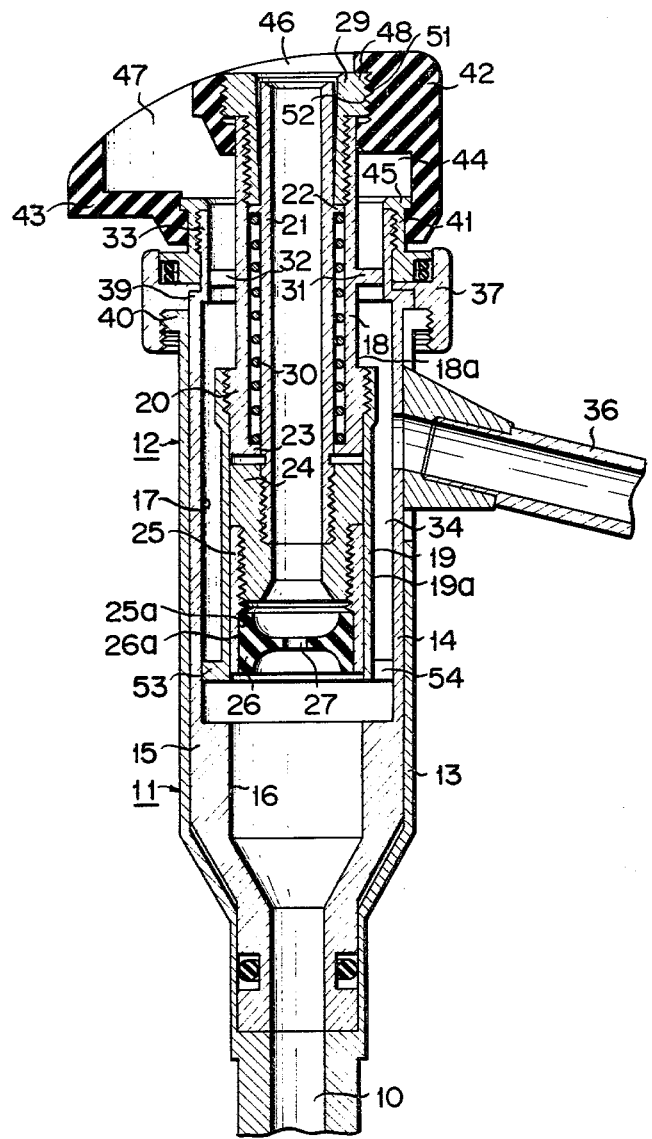
FIG. 6 shows a longitudinal cross sectional view of another embodiment of this invention.

In an embodiment shown in FIG. 6 a stop ring 29 includes a flange 48 having external screw threads 51 which engage internal screw threads 52 provided on the inner annular recessed wall of a first air inlet 46. In this arrangement a cap 42 can be attached to a stop ring 29 as in the case of the embodiment of FIGS. 2, 4 and 5 in which a snap engagement is used. A radially outwardly extending flange 53 is integrally formed on the distal end of a second tubular member 19. The outer surface of the flange 53 is slidably fitted in the increased inner surface of a hollow cylindrical member 14. A plurality of passages 54 are formed in the flange 53 at its circumferential intervals. The passages 54 correspond to the hole 35 of the preceding embodiment.

Figure 7:
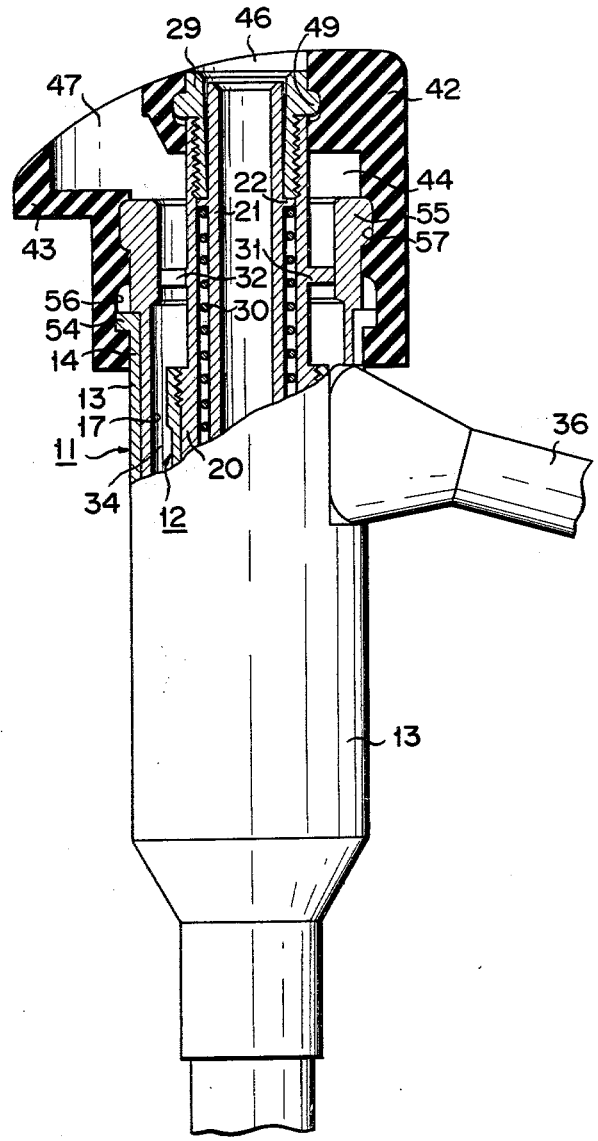
FIG. 7 shows a partially broken front view of a further embodiment of this invention.

In an embodiment shown in FIG. 7, flanges 54 and 55 are provided on the proximal ends of a mounting tube 13 and hollow cylindrical member 14, respectively. The flanges 54 and 55 make a snap engagement with corresponding annular grooves 56 and 57 in a cap 42, respectively. In this embodiment, the cap 42 can be sealingly mounted directly on an outer tube assembly 11 and there is no need for a mounting ring and connector as used in the preceding embodiment. This assures a simpler construction.

What is claimed is:

1. A suction control device in an endoscope comprising:
    an outer tube means mounted in an operation section of an endoscope and having a distal end and a proximal end, said distal end communicating with an endoscope channel extending in the endoscope;
    an inner tube means inserted into the outer tube means for communicating with the endoscope channel and having a distal end portion and proximal end;
    an elastic sealing member mounted in the distal end portion of the inner tube means and having a central aperture with a diameter of an elongated medical instrument to be inserted into the endoscope channel;
    an air chamber defined between the outer tube means and the inner tube means for communicating with the endoscope channel;
    a suction pipe extending outwardly from the outer tube means for communicating with the air chamber; and
    an elastic, flexible cap sealingly mounted on the proximal end of the outer tube means and the proximal end of the inner tube means and having a first inlet communicating with the inner tube means and a second inlet communicating with the air chamber, said first inlet and said second inlet being arranged adjacent to each other so as to be blocked simultaneously by a finger cushion.

2. The control device according to claim 1, wherein said cap has an overhanging portion extending outwardly radially of said outer tube means, and said second air inlet is formed in said overhanging portion.

3. The control device according to claim 1, wherein said sealing member has a substantially H shape in a longitudinal cross section thereof and has an outer surface sealingly connected to the innermost surface of said inner tube means.

4. The control device according to claim 3, wherein said central aperture of said sealing member is provided in the horizontal bar portion of said H shape and extends perpendicular thereto.

* * * * *